(12) United States Patent
Vignisson et al.

(10) Patent No.: US 11,547,345 B2
(45) Date of Patent: Jan. 10, 2023

(54) DYNAMIC NEUROPSYCHOLOGICAL ASSESSMENT TOOL

(71) Applicants: Vidar Vignisson, San Diego, CA (US); Gregory Sahagian, Solana Beach, CA (US)

(72) Inventors: Vidar Vignisson, San Diego, CA (US); Gregory Sahagian, Solana Beach, CA (US)

(73) Assignee: Intraneuron, Solana Beach, CA (US)

( * ) Notice: Subject to any disclaimer, the term of this patent is extended or adjusted under 35 U.S.C. 154(b) by 414 days.

(21) Appl. No.: 16/866,068

(22) Filed: May 4, 2020

(65) Prior Publication Data

US 2020/0345290 A1 Nov. 5, 2020

Related U.S. Application Data

(60) Provisional application No. 62/843,425, filed on May 4, 2019.

(51) Int. Cl.
| | |
|---|---|
| *A61B 5/00* | (2006.01) |
| *G10L 15/26* | (2006.01) |
| *A61B 5/16* | (2006.01) |
| *G16H 10/20* | (2018.01) |
| *G16H 10/60* | (2018.01) |

(Continued)

(52) U.S. Cl.
CPC .......... *A61B 5/4088* (2013.01); *A61B 5/0022* (2013.01); *A61B 5/163* (2017.08); *A61B 5/165* (2013.01); *A61B 5/4803* (2013.01); *A61B 5/7203* (2013.01); *G10L 15/26* (2013.01); *G16H 10/20* (2018.01); *G16H 10/60* (2018.01); *G16H 15/00* (2018.01); *G16H 50/20* (2018.01); *G16H 50/30* (2018.01); *G16H 80/00* (2018.01)

(58) Field of Classification Search
CPC ..... A61B 5/4088; A61B 5/163; A61B 5/0022; A61B 5/165; A61B 5/4803; A61B 5/7203; G16H 10/60; G16H 15/00; G16H 50/30; G16H 50/20; G16H 10/20; G10L 15/26
USPC .......................................................... 600/558
See application file for complete search history.

(56) References Cited

U.S. PATENT DOCUMENTS

| 10,748,439 B1 * | 8/2020 | Glenn ..................... G09B 7/00 |
| 2014/0163426 A1 * | 6/2014 | Alberts ................ A61B 5/4023 600/595 |

(Continued)

*Primary Examiner* — Kerri L McNally
(74) *Attorney, Agent, or Firm* — Kenyon Jenckes

(57) ABSTRACT

A dynamic neuropsychological assessment tool according to an embodiment utilizes speech recognition, speech synthesis and machine learning to assess whether a patient is at risk for a neurological disorder, such as Alzheimer's disease. The dynamic neuropsychological assessment tool enables self-administration by a patient. The tool performs pre-test validation operations on the test environment, test equipment, and the patient's capability for performing the test at that time. The tool also enables dynamic modification of a questionnaire presented to the patient while the patient completes the questionnaire. Also provides the dynamic modification of which tests to present the patient with. The modification can be rule based or modified by a provider. The dynamic neuropsychological assessment tool enables providers and administrators to modify and improve tests and validate them using machine learning based on previously completed assessments and results.

15 Claims, 6 Drawing Sheets

(51) Int. Cl.
  *G16H 50/20* (2018.01)
  *G16H 50/30* (2018.01)
  *G16H 15/00* (2018.01)
  *G16H 80/00* (2018.01)

(56) References Cited

U.S. PATENT DOCUMENTS

| | | | |
|---|---|---|---|
| 2016/0125748 A1* | 5/2016 | Ashford | G16H 40/63 |
| | | | 434/236 |
| 2017/0053540 A1* | 2/2017 | Meagher | G09B 5/00 |
| 2017/0365101 A1* | 12/2017 | Samec | G16H 50/20 |
| 2018/0322961 A1* | 11/2018 | Kim | G16H 80/00 |
| 2019/0167179 A1* | 6/2019 | Arzy | A61B 5/7475 |
| 2019/0304090 A1* | 10/2019 | Wang | G06K 9/6287 |
| 2020/0365275 A1* | 11/2020 | Barnett | A61B 5/4088 |

* cited by examiner

DYNAMIC NEUROPSYCHOLOGICAL ASSESSMENT TOOL

TECHNICAL FIELD

Described herein is a dynamic neuropsychological assessment tool that utilizes speech recognition, speech synthesis, and machine learning to assess whether a patient is at risk for a neurological disorder.

BACKGROUND

The prevalence of cognitive disorders, such as Alzheimer's disease, is increasing as the population ages. Many cognitive disorders evolve in the patient over several years before clinical manifestations occur. Early and accurate detection of cognitive disorders benefits research and clinical practice. Accurate detection may facilitate improvement in drug outcome through the enrollment of appropriate study participants. For example, inaccurate diagnosis of Alzheimer's disease may contribute to the 99% failure rate among stage III drug trials. Early and accurate detection benefits patients, caretakers and families by facilitating access to appropriate therapeutics.

In the earliest phases of cognitive disorders the clinical standard of care is prone to misdiagnosis. An increasing shortage of neurologists and neuropsychologists is resulting in delayed diagnosis and care.

Physicians and the general public have no easy way to accurately detect and diagnose cognitive disorders. The majority of primary care physicians are not screening patients for cognitive disorders. The financial burden of Alzheimer's disease and other neurological disorders is staggering and increasing. Early detection is shown to result in substantial cost savings.

Current neuropsychological tests require a test administrator trained in assessment and interpretation, and are currently performed with pen and paper and administered by a test administrator. A test administrator is required for both computerized tests and manually administered pen and paper tests.

Patients must visit a location where a test administrator can administer a test. The location is usually a neurology office. Primary care physicians are usually not equipped to administer neuropsychological testing. This prevents some patients from being tested and delays testing for others.

Current computerized neuropsychological tests require the user to utilize a pointing device and a keyboard for every test. The requirement of a pointing device and keyboard is a barrier to some elderly people, as they may not be computer savvy. The testing performs no readiness validation of the user and/or testing equipment or testing environment. Therefore, the quality of the testing is not always ideal and there is no way to determine whether test conditions are sufficient.

The current administration of neuropsychological tests presents a burden on the physician and the physician's staff, because they have to administer the tests to the patient. This consists of telling the patient the instructions for each test, possibly reading out words/phrases/digits and recording responses, timings, etc. Once the test is completed, the test administrator has to look at tables or use a formula to convert the results they recorded into a normalized score. This also presents a burden to patients in that they have to schedule appointment(s), travel to and wait at a medical facility to take the test, and meet with someone to administer the test.

Although there are chemical precursors and tests that can identify the onset of Alzheimer's disease, such as amyloid precursor precursors, for early testing has shown to provide improved evidence for early detection.

Accordingly, there is a need for a reliable neuropsychological testing system that enables the patient to self-administer the test where and when the patient desires.

SUMMARY

The dynamic neuropsychological assessment tool enables providers, patients and family members to screen for the presence of neurological disorders. Patients complete a questionnaire and software based neuropsychological screening.

The dynamic neuropsychological assessment tool provides the ability to perform a pre-test validation of the suitability of the test environment, test equipment, and patient capabilities for testing at that time. The patient can perform the neuropsychological screening with the software assessment tool independently, i.e., self-administration. Therefore a test administrator is not required.

The neuropsychological assessment tool generates a report providing information on the likelihood of the risk or presence of a neurological disorder and facilitates the planning for further evaluation and referral.

DETAILED DESCRIPTION

In an embodiment, a dynamic neuropsychological assessment tool provides pre-defined testing batteries that are disease specific. For example, a pre-defined battery specific to diagnosing Alzheimer's disease is described. The testing battery consists of a questionnaire and tests that measure different aspects of brain functioning that when combined provide a high sensitivity and specificity to Alzheimer's disease.

Each individual test can indicate cognitive impairment, but by themselves may not provide great sensitivity and specificity to Alzheimer's disease or any specific disease.

There are well-known test batteries that combine a range of tests to provide an overview of cognitive skills. These are good early tests to rule out problems in certain functions and provide an indication of functions that may need further testing. But, none of these testing batteries are disease specific or aim to diagnose a specific disease.

A number of factors can impact the quality of neuropsychological testing. For example, the patient may be tired or hungry or suffering from another ailment. The volume of speakers, brightness of monitors, etc. may not be adequate for the patient to hear or see or the patient may not be able to read or write. Furthermore, with the current coronavirus epidemic, research facilities and doctor's office may be closed, and elderly patients may not care to travel in public due to possible invention Current computerized neuropsychological tests do not try to determine whether these or other factors may impact the test.

A dynamic neuropsychological assessment tool according to embodiment may perform numerous validation tests. All results are recorded for future evaluation. Furthermore, all voice interactions are recorded and can be reevaluated. The testing can also be performed at the patient's home using an OTS (off the shelf) computing pad or smart phone with a simple user interface (UI) to enhance the user experience, and avoid interaction with other people.

Figure 1:
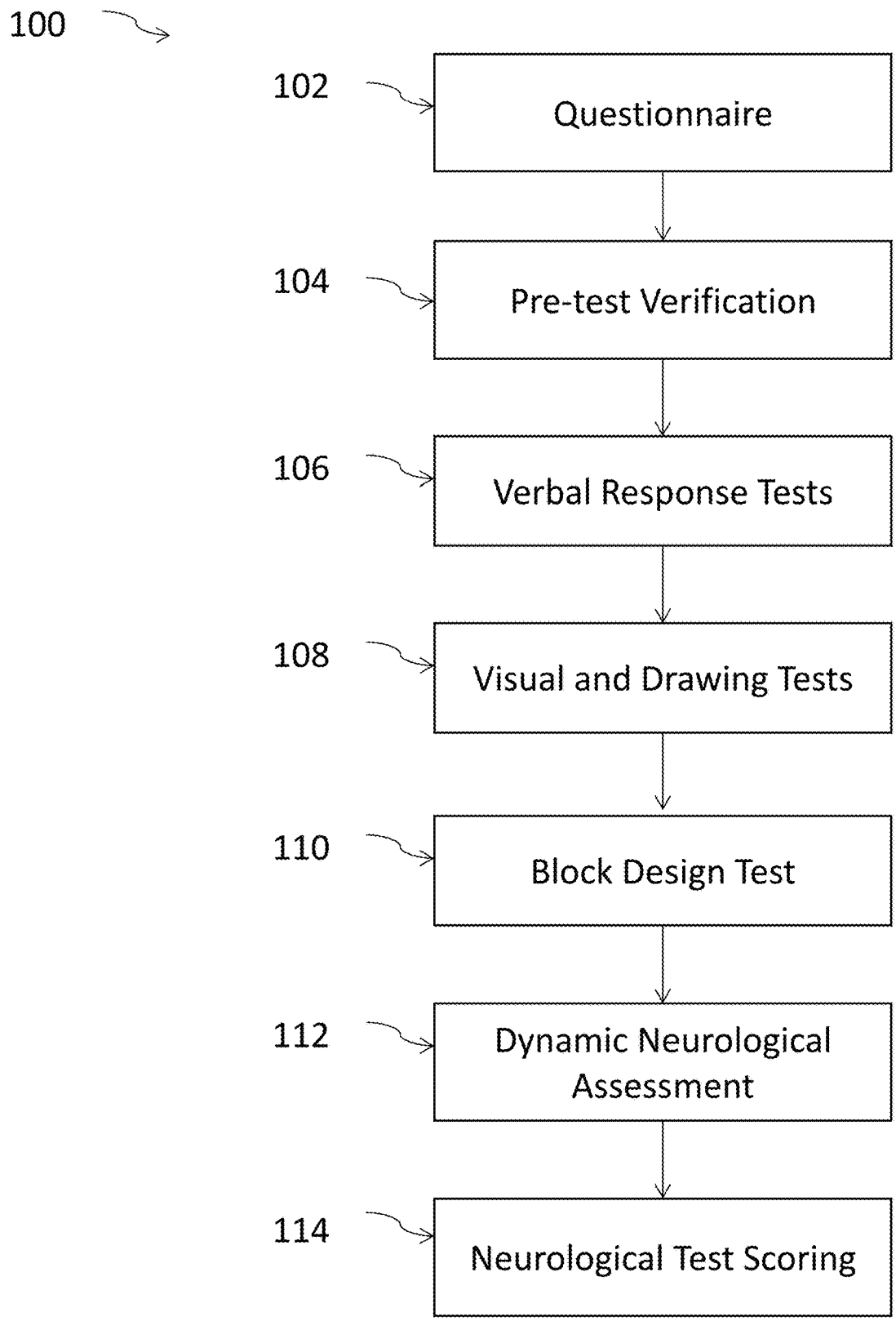
FIG. 1 is a flowchart showing an exemplary testing procedure that can be implemented using the neuropsychological assessment tool.

FIG. 1 is a flowchart describing an exemplary testing procedure 100. In 102, the dynamic neuropsychological assessment tool can ask the patient to complete a questionnaire to determine whether the patient is prepared to take the test. Questions may include, for example, whether the patient had a good night's sleep, since being tired affects cognitive ability, or ate a good breakfast, since hunger can distract and impact concentration. Other questions may include whether the patient drank anything with alcohol in it or consumed any medication, such as sleep medicine, the night before the test, as that could impair the patient's ability to test.

The provider can set a rule that the test needs to be postponed based on the answers to the questions. So, the questionnaire can be used as a further validation tool.

The questionnaire may also includes questions that help with scoring the neuropsychological tests. Demographic populations, based on age, gender, education level, native language, etc., may perform differently on neuropsychological tests. Therefore, asking questions related to demographics enables better scoring by normalizing scores to the appropriate demographic.

The exemplary dynamic neuropsychological assessment tool questionnaires can also be performed completely using a voice user interface, limiting the amount of computer knowledge required of patients, thereby eliminating the need for a test administrator and for the patient to have to travel to a medical facility to take the test.

The dynamic neuropsychological assessment tool can assess the patient to determine whether the patient has adequate eyesight to read text on the screen and whether the screen is bright enough, has adequate hearing to hear text played via speaker or the volume of the speaker is loud enough, has adequate mobility to draw a line on a screen, speaks clearly and with sufficient volume for effective speech recognition, i.e., speech recognition with a low error rate and high confidence, and/or can follow directions played through a speaker or displayed on a screen.

The validation can also determine if background noise interferes with the test taking. Most speech is above 50 db, so if audio is detected above a threshold (e.g., 50 db) and cannot detect speech in it using speech recognition software, there is likely too much background noise to perform the test.

Other technical issues may relate to the hardware and software being used, such as browser integrity, app or OS capability. For people do not have equipment that can run sufficiently the testing on browsers or operating systems, instructions or call centers may be used to sufficiently upgrade them.

The provider can set a rule that the test needs to be postponed based on the results of the various tests. Or the patient, or a local attendant, e.g., nurse or family member, could be taken through a process to have equipment sent or they could speak with a person for help.

In 104, the dynamic neuropsychological assessment tool may perform an automated pre-test validation. Neuropsychological test taking requires an appropriate environment with equipment that meets the requirements of the tests being taken. Patients must also be able to hear, understand the language the test is taken in and have other abilities required of the tests.

Figure 5:
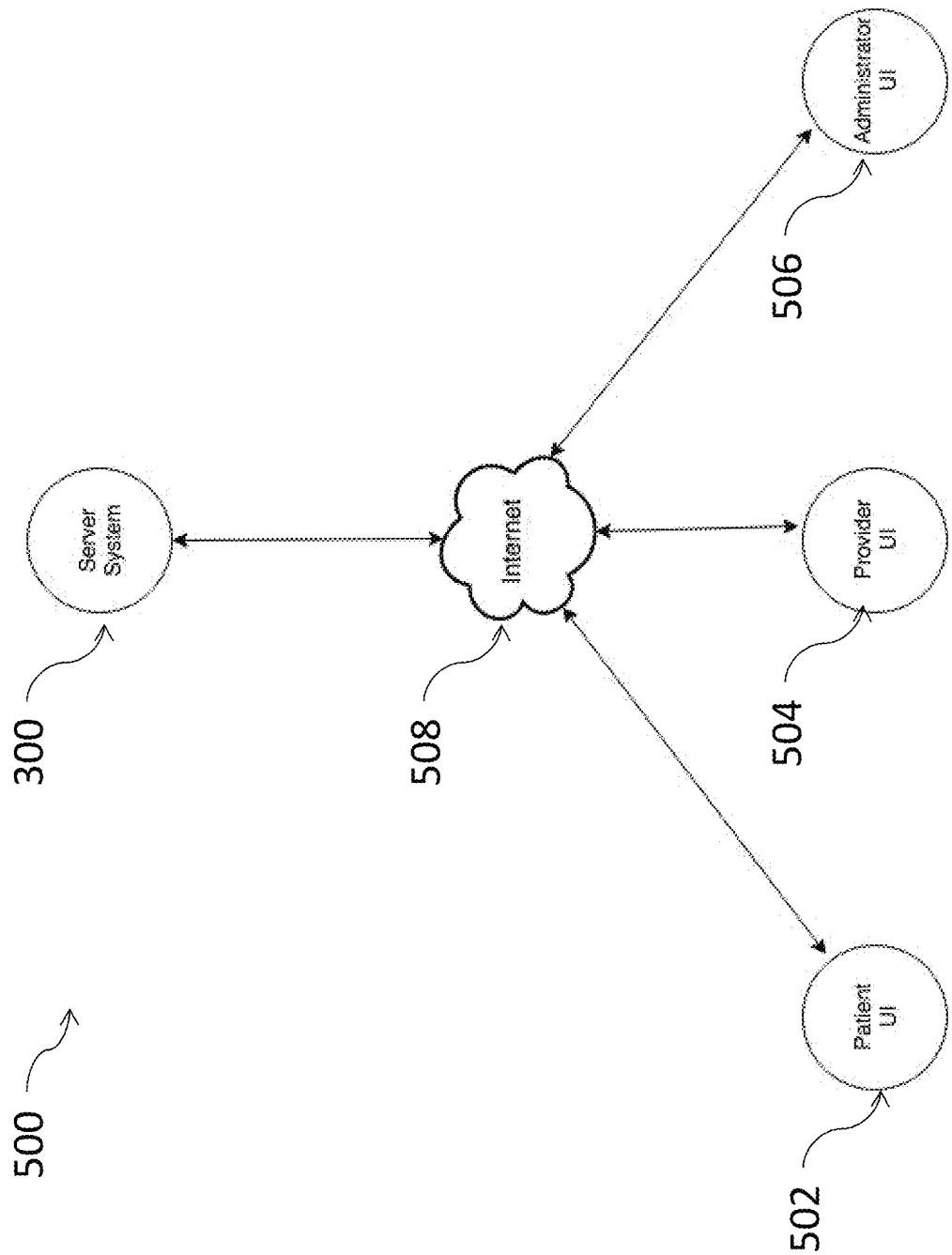
FIG. 5 shows an exemplary system diagram for implementation of the neuropsychological assessment tool.

In order to successfully test patients and provide accurate results, the Patient UI 502, shown in FIG. 5, provides the ability to include pre-test validation. Equipment requirements for the Patient UI may include hardware typically available on a tablet computer such as a microphone for speech recognition, a speaker for audio output, and a touch screen for drawing and writing.

The environment a user is in may not be conducive to taking a test, due to noise and/or other distractions. Equipment may not provide all necessary capabilities and/or may not function properly. Furthermore, in the current state of the coronavirus epidemic, it my result in unwanted contact and/or infection.

Figure 2:
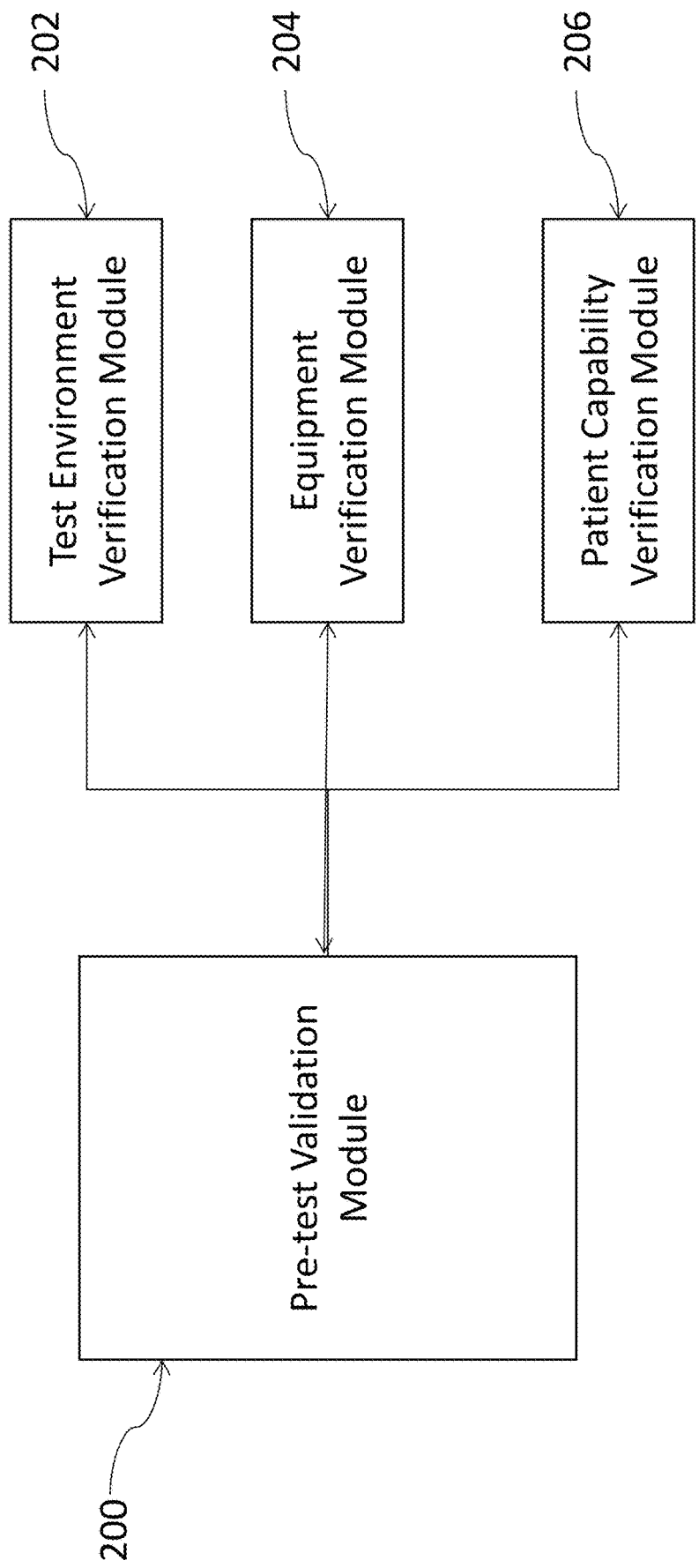
FIG. 2 is a block diagram of a pre-test validation module for the neuropsychological assessment tool according to an embodiment.
Figure 3:
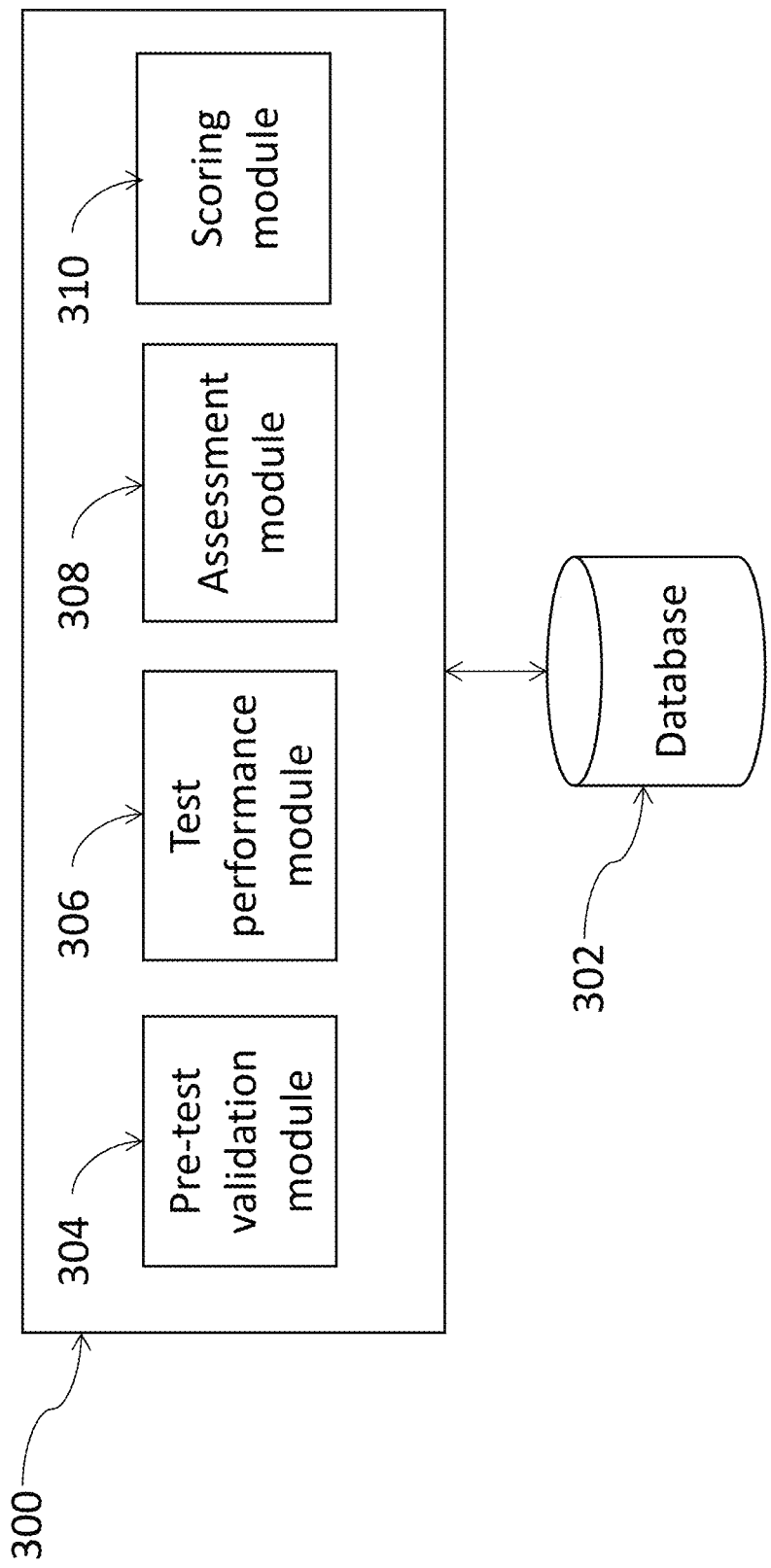
FIG. 3 is a block diagram of a server system for the neuropsychological assessment tool according to an embodiment.

FIG. 2 shows a pre-test validation module 200, which may reside on a server 300 in communication with a database 302, as shown in FIG. 3. The pre-test validation module 200 includes a test environment verification module 202 to determine if the test environment is suitable.

Factors that may impact test environment suitability include having too many people present, too much noise, flashing lights, etc. This can be tested by recording a video on the testing device, e.g., a tablet-type computer, and performing video analysis and validation. Prior to validation, a machine-learning algorithm can be trained with videos that do not meet environmental criteria and with videos that do meet the criteria. The machine-learning algorithm can then evaluate the recorded video to determine whether it belongs to the videos that do not meet the environment criteria. There can also be a link to a person via video chat, for them to verify that the testing is ready.

The test environment verification module 202 can also determine whether there is too much noise in the test environment and whether the microphone and speakers function properly.

The testing device can play known audio, record the audio played, and determine the level of noise/distortion, i.e., the quality of audio distortion due to the environment, using a well-defined algorithms to arrive at score. Some algorithms that can be used include Perceptual Evaluation of Speech Quality (PESQ), Perceptual Objective Listening Quality Assessment (POLQA), Perceptual Evaluation of Video Quality (PEVQ), Perceptual Evaluation of Audio Quality (PEAQ), and Hearing-Aid Speech Quality Index (HASQI). The scores for the algorithm(s) used can be compared to a threshold. The threshold can be configurable by the Provider UI 504 and/or Administrator UI 506, shown in FIG. 5.

Another approach is to ask a question from the questionnaire, i.e., what is the patient's birth date, and then displaying the birth date on the screen and asking if that is correct. If the answer is yes, the speech recognition can be considered to be working.

An equipment verification module 204 can be used to make sure the microphone and speakers work, if speech synthesis and speech recognition is needed. This can be accomplished by playing and recording audio or by having the patient listen and have their speech recognized. The equipment verification module can also make sure touch screen is present and works, if tests require drawing. This can be accomplished by having the patient touch the drawing surface.

A patient capability verification module 206 can be used to verify the patient's ability to see, read, speak and hear adequately to complete the test. This can include making sure patients can read text on screen and speak adequately.

In an exemplary verification operation, the patient will read pre-determined text displayed on the screen. The system will record the audio and/or stream the audio to speech recognition. The speech recognition will transform the audio to text. The system will then compare the pre-determined text to the recognized speech to determine how accurate the patient reading was.

To make sure a patient can hear audio, the patient capability module can have the patient repeat back what was heard. In an exemplary verification operation, the patient will listen to pre-determined text displayed on the screen. The system will record the audio and/or stream the audio to speech recognition. The speech recognition will transform the audio to text. The system will then compare the pre-determined text to the recognized speech to determine how accurate the patient reading was.

To make sure a patient can touch a tablet and has no physical limitations that prevent it, the patient capability verification module 206 can display an image on the tablet screen and request the patient touch it.

The dynamic neuropsychological assessment tool provides neuropsychological tests that can be self-administered, thereby eliminating the need for a trained test administrator. Therefore, they can be performed both in a clinical and a non-clinical setting.

Self-administration of the tests can be achieved through the use of speech recognition, speech synthesis and touch-based screens, sensors, machine learning and other technology.

When a patient takes a dynamic neuropsychological assessment tool test the computer speaks instructions that are played through a computer speaker and captures responses from the patient. The computer is playing a state machine that was generated based on the test battery assigned to the patient for the given session.

The state machine may have an associated stack. If an event is detected (i.e., the patient is interrupted) or a keyword that performs an out of band action is spoken (e.g. "help"), the current state is saved to the stack. A sub-state machine is then played starting with a start-state that is associated with the out of band event, whether initiated by a detected event or a pre-defined keyword. When the sub-state machine completes executing, the most recent state is popped from the stack and its execution continues.

Basic computer capabilities, such as speakers, microphone, a pointing device, color display screen are sufficient to handle self-administration of most neuropsychological tests.

Once the pre-test validation has been performed, verbal response test(s) 106 may be administered. Recognizing speech and processing the spoken responses using a Voice User Interface (VUI) enables the self-administration of a large number of neuropsychological tests. This includes memory recall tests, describing how two objects are similar, verbal learning and fluency tests, naming objects in pictures, repeating words or digits and many more. A speaker and microphone is also sufficient to provide self-administered audio based tests that require tones, or counting of tones.

Visual and drawing test(s) 108 may also be administered. Pointing devices, whether a mouse or a touch screen with or without a stylus, enable self administration of drawing tests, sorting tests, indicating missing pieces of a picture and many more. A selection is frequently sufficient to provide an answer in these tests.

Symbol search and coding can also be performed using a pointing device. Trail making can be performed with a pointing device.

Machine learning can determine characteristics of drawings, through training using pictures from past tests. For example, which parts of an analog clock were drawn? The machine can learn to determine how close to a form, shape, pattern, and arrangement a drawing is and/or which elements are missing. This will provide a more objective interpretation than an interpretation by a human.

The block design test 110 requires the patient to put together, e.g, red-and-white blocks in a pattern according to a displayed model. This is timed, and some of the more difficult puzzles may award bonuses for speed.

There are software-only approaches that can be use to implement the block design test. Block design tests can be emulated on a screen, with the patient using a pointing device to drag and reorient blocks into appropriate patterns. Using a video camera, the pattern and layout of the blocks can be determined by processing the video. Using a camera without video capabilities, the pattern and layout of the blocks can also be determined by processing images.

In another embodiment, custom blocks are used that have capacitive pads that can be detected on a capacitive touch screen. Each block with the red and white patterns will have a configuration of capacitive pads that are unique to that color and pattern. The dynamic neuropsychological assessment tool will detect each block placed on the screen and its orientation. The blocks can have the pads on every side, so that any side can be detected.

The patient places the blocks on the touch screen to match the patterns in the test and the dynamic neuropsychological assessment tool will determine if the pattern was matched or not.

The current system enables dynamic neurological assessment 112. Current computerized neuropsychological testing does not utilize speech recognition, speech synthesis and machine learning to provide a more dynamic and improved user experience.

Test designers can modify the instructions and other voice prompts played during a test, which, unlike current systems for computerized neuropsychological testing, enables the test designed to modify the test battery while the user is taking the test.

FIG. 3 shows an overview system of the neuorpsychological assessment tool 300 according to an embodiment. Data from the various assessment tools are stored in the database 302. Pre-test validation module 304, test performance module 306, assessment module 308, and Scoring module 310 are all stored for further processing.

Once all of the tests have been completed, the dynamic neuropsychological assessment tool produces test score(s) 114. Current computerized neuropsychological testing does not provide a single combined score that is created based on the percentile rank of the patients results on the other tests within the battery and the weight of each test within the battery.

In an embodiment, raw scores from neuropsychological tests are normalized based on parameters such as age, education, gender, etc. The score can then be converted to a percentile rank, so that all scores can be presented on a scale from, e.g, 0 to 100.

Figure 4A:
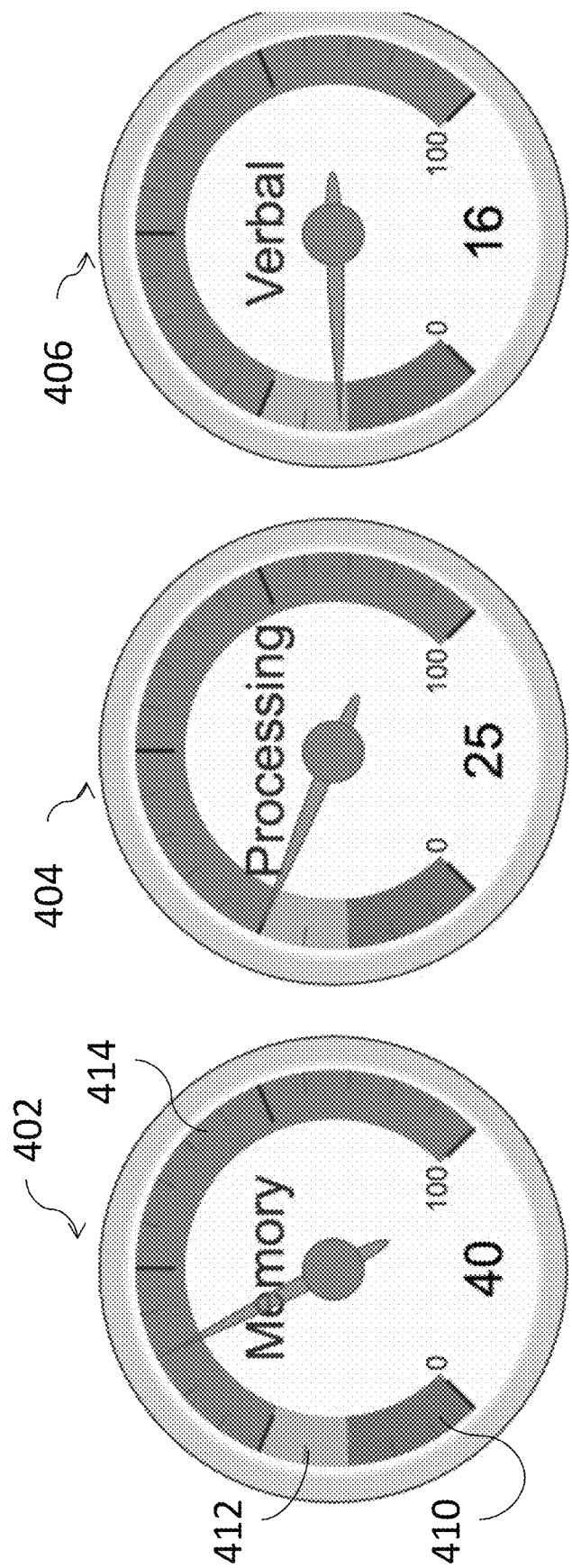
FIG. 4A shows exemplary test score presentations.

Each neuropsychological test provides data on a different aspect of brain function. As shown in FIG. 4A, in an embodiment, scores are represented using colors, where red 410 indicates high risk, yellow 412 indicates concern and green 414 indicates that the person is within an acceptable range, with different virtual gauges 402, 404, and 406 representing memory, processing, and verbal scores, respectively.

Figure 4B:
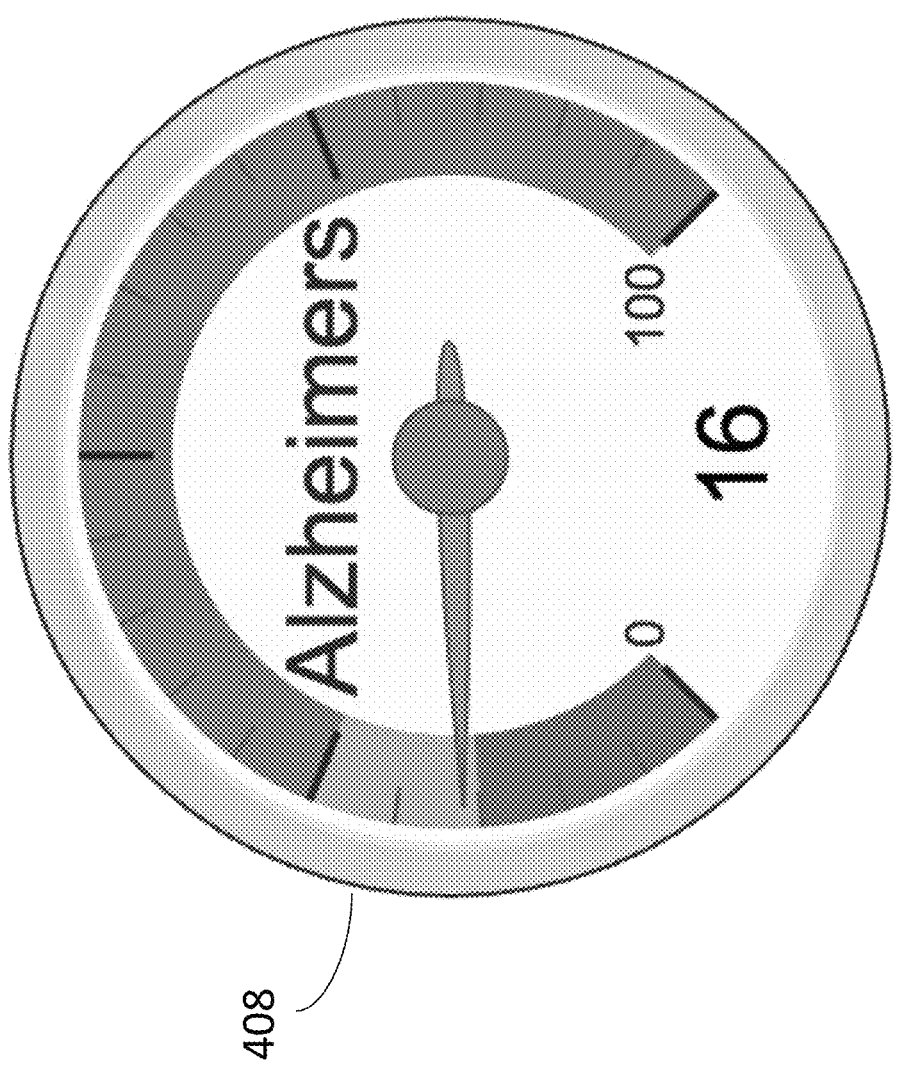
FIG. 4B shows another exemplary test score presentation.

For a given disease, such as Alzheimer's, the results of the tests can be converted to a single number between, e.g., 0 and 100, as shown by gauge 408 in FIG. 4B. The number is converted based on weight for each number and in some instances. This would be the patients Alzheimer's Number.

Customized tests require normalized data as well. Test designers using the state machine can upload their normalization data to automatically score those tests. Pre-defined tests already have their scoring functions included within the system.

The the dynamic neuropsychological assessment tool enables providers to create, design and administer their own tests.

Furthermore, the provider can create test batteries that are different based on rules that utilize results from previous tests within the same test battery. The dynamic neuropsychological assessment tool provides the ability to design customized tests and include them in a test battery for comparison and validation with other existing tests.

The the dynamic neuropsychological assessment tool offers dynamic questionnaires that provide data that is not only collected, but can be utilized in scoring. Provider created questionnaires consisting of provider defined named fields, whose value can be utilized in scoring functions.

In addition, the\dynamic neuropsychological assessment tool provides an event based state machine with specific features to simplify designing neuropsychological tests.

This functionality also enables the creation of automated decision trees, where the patient is administered tests corresponding to information obtained during the session and the provider is provided with relevant information during the session. The session is dynamically configured based on events that occur during the session.

The state machine is equivalent to a Turing machine, of course limited by the physical limitations of the hardware the state machine executes on. A Turing machine is a theoretical computer that can compute anything that is computable on a computer, and being theoretical has as unlimited memory.

Many OTS AIs and state machines are available from different suppliers, and may provide different standards of performance for different purposes.

The state machine can be considered a virtual instruction set that the tests get compiled to. The resulting instructions can be executed on the client side in the test equipment to implement the tests. This provides flexibility, as the administrator or provider can essentially program state machines to create new tests via the administrator UI 506 or provider UI 504.

A battery consists of an ordered group of activities where each activity type can occur zero or more times. Activity types can include Readiness Validations, Examinations, Rating Scales, Questionnaires, and Neuropsychological tests. A battery can be assigned to a patient as part of a session. The battery can then be sent to the patient. The patient can follow the steps in the battery to complete the activities belonging to the battery, and any other activity that can be programmed via the state machine instruction set.

A battery plays all of its activities in order, when it is started. The battery player checks each activity to see if it is ready. Activities that are not ready are skipped if there are other activities that are ready to play.

An activity can have an associated timeout. If a timeout is associated with an activity, a timer is set and play continues when the timer expiration event fires.

Every activity knows how to play itself. An activity can be in a ready state, not ready state or completed stated. If an activity is in a not ready state it may have an associated timeout.

A battery can be dynamic, in that the activities assigned to a patient can be modified, while the patient is completing activities in the test. A battery can also be dynamic based on results within the test.

A short simple test can determine areas of likely cognitive impairment. A set of rules can add tests for the patient to further explore that impairment. Potentially resulting in a likely diagnosis of a given disease, i.e. the short test, would add the early Alzheimer's battery, if scores were poor on the short test in the areas that correspond with what is tested in the early Alzheimer's battery.

New tests can be developed utilizing the state machine. The effectiveness of the tests can be determined by adding them to a battery of other tests that already have norms. Those considered sufficiently effective can be provided as an alternative to the existing tests.

This could enable the use of shorter tests with greater specificity and sensitivity for a given disease.

The rules may utilize a state machine to perform actions based on transitional conditions that can be performed based on data collected during the execution of the battery. The state machine is programmable via the provider UI 504.

Programming of the state machine consists of creating a test and associated trials. Each trial is then implemented/compiled as instructions for the state machine. The state machine program is defined through states, actions and transitions. States have unique names. An ordered list of actions is associated with each state. Transitions are associated with events and states.

Detected events, such as interruptions and keywords recognized from speech result in the execution of sub-state machines.

For example, if an audio end event fires a transition may be found to transition to a new state. A more sophisticated example would be a state with a recognition action, where the grammar is yes and no. When a speech is recognized a result event is fired. The result event will find a transition for the given state and the result event and perform the associated transition.

An interruption event is determined to have occurred when a sequence of words or phrases that is not in the recognition grammar is detected. An interruption has occurred when a sequence of words not in a grammar is greater than a threshold, without any words from the grammar being recognized. An associated action is then performed that can result in the execution of a sub-state machine.

All data and timings from the state machine can be stored persistently, such as the timing of transition events, the interim results and final results of speech recognition, etc.

Higher-level refinements of the state machine make it simpler for providers to create their own tests.

Such as a delayed recall state group where a sub-state machine consisting of a state machine where a list of words is played to the user and recognized or a delayed recognition state, where a list of words is played for the patient and for each word the recognizer looks for a yes or a no, etc.

The dynamic neuropsychological assessment tool provides the ability for providers to enter text phrases that are synthesized into speech. The provider selects a language for the text and enters parameters that impact the speech synthesis.

The system generates a Speech Synthesis Markup Language (SSML) representation of the text. The provider has the ability to edit the SSML, if they so desire.

The system then synthesizes the speech and saves the result as an audio file. The provider has the ability to play back the audio file and repeat the process until they are satisfied with the result.

The resulting audio file can then be associated with an audio action, which can be associated with a state in the state machine. The state machine knows how to play the audio associated with the action.

The dynamic neuropsychological assessment tool provides the ability for providers to enter word lists and text phrases that can be converted into a grammar for a speech recognizer.

The provider can select a speech recognition engine, since some speech recognition engines perform better on different grammars, such as numeric versus verbal.

The provider can also select the language the grammar belongs to and the speech recognizer should be configured to use.

This data can be associated with a speech recognition action, which can be associated with a state in the state machine. The state machine knows how to perform the recognition function.

Speech that is recognized goes through a sanitation process. The speech recognizers can detect whether there are multiple speakers. The system takes this into account and attempts to filter out the speaker that is not taking the test.

The recognized speech is also corrected for known speech recognition issues, such as recognizing hut as hot and recognizing numbers as a word instead of a digit. The known speech recognition issues depend on the grammar being used for speech recognition.

When the speech recognizer discovers words that are not in the grammar that is being recognized, it uses a machine-learning model to determine whether the words represent a command, an interruption or not.

Questionnaires vary from provider to provider and for many other reasons. Providers place different emphasis on different questions. There are still some questions that are required to accurately score tests.

Questionnaires are a collection of questions. Each question has an associated type, that determines how answers are validated and questions are presented as fields. There is an option to use audio, to ask the question and recognize an answer.

Questions can be named for processing in state machine and they can be tied to an existing named field in the patient database schema.

The values of answers can be used in transitional conditions through a reference to the name.

Certain data fields or questions are required for scoring tests. These fields vary depending on the neuropsychological tests that are in the battery. Sure as the date of birth field that can be used for normalizing scoring for a test.

Scoring of tests consists of converting raw scores to normalized scores. Converting the scores requires parameters, such as age, education level, gender, etc.

Age is generally collected as date of birth, in order to be able to calculate the age of a patient at the time of any session and not request it repeatedly.

Neuropsychological data fields have predefined names that a question can be associated with.

A session consists of all the activities that are performed by a provider and patient during a single interaction.

An interaction could be a visit to an office where the patient is evaluated by a provider, it could consist of activities that patient performed at home, it could consist of activities that the provider performed on their own or any combination there of.

The provider determines what belongs in each session.

Any sessions with a patient can be named and saved as a template. When a provider creates a new session, they can then select the session template to create the session.

All configurations, examinations, diagnosis, procedures, assessments, recommendations, tests and anything else the provider entered or assigned during the session are copied to the new session.

The provider can adjust the values for all activities on a single page. This reduces the need for data entry during time with the patient and reduces the amount of time required to prepare for the session with the patient.

Patients with a similar or identical session history, for example the same diagnosis and procedures, and similar or the same session data are likely to be on the same path.

Given the session data of many patients, what activities will take place in a new or next session for a given patient can be predicted. We can also predict values for each of the activities during the new session. From a machine learning perspective, the system is predicting that a particular event is likely to be followed by another event.

When a new session is created without the aid of a session template, the default configuration and initial values are predicted. Mapping the patients previous sessions to features and inputting them into a machine learning model creates the predictions.

The machine-learning model has been iteratively trained with data from previous sessions, in order to predict the sequence of events and therefore the values in the following session.

The dynamic neuropsychological assessment tool provides capabilities to the following primary user groups: patients; providers, and administrators Patients have access to battery of activities where they answer questions, and perform neuropsychological assessment.

Providers only have access to patients that they have permissions to see. Providers automatically have access to patients that they create. They can also grant others access to those patients.

Providers can direct all aspects of the system through a Voice User Interface (VUI). This frees them during patient interaction, from pointing, clicking and typing.

Administrators have access to all aspects of the system. The system is made up of multiple components that organize the functionality of the system and provide the services required to assess patients, manage their data and configure everything.

Every component has a set of configuration capabilities, and example of which is outlined below:
Session Management
    Configuration and Assignment
    Diagnosis
    Medication
    Patient Battery Creation/Configuration of disease specific batteries.
  Examinations
  Rating Scales
  Questionnaires
  Neuropsychological Testing
    Readiness Validation
    State Machine Player
    Tracking
  Assessment
  Description
  Examinations
  Rating Scales
  Questionnaires
  Neuropsychological Testing
    Readiness Validation
    State Machine Player
    Tracking
  Recommendation
  Procedures
  Injections
  Report
  Data Collection
  Result Presentation
Patient Management
Provider Management
  Permissions
  Provider
  Provider Groups
  Logging
Insurance Management
Administrative Management
  Data Export
  Anonymized aggregate reporting FIG. 5 shows an exemplary communication system 500 for the dynamic neuropsychological assessment tool. The system includes the server system 300, Patient UI 502, Provider UI 504, and Administrator UI 506. All components can interact through a networked computer system, e.g., the Internet 508.

The server system 300 may provide services required by the Patient UI 504 and Administrator UI 506. The server system also implements reporting, analytics and integration with the 3rd party services.

The Administrator UI 506 enables users with administrative permissions to configure all functions of the system and perform all functions of the system. The Administrator UI includes all functions of the Provider and Patient UIs. The administrator UI provides the ability to create, read, update and delete (CRUD) any component within the system.

The Provider UI 504 enables providers to configure, view and edit the functions of the system they have permissions to access. The Provider UI provides simplified functions of the Administrator UI. The Provider UI is restricted to functions that apply to the set of patients that the provider has permissions to access.

Reports may be generated for a session from the activities during that session. Such as from the patient going through a testing battery.

In addition providers can provide additional information within the report to better communicate with the patient and other providers.

In the sections for Situation, Background, Assessment and Recommendations providers can select pre-defined statements that they want included in the report, in addition to being able to enter free form text. Providers also have the ability to manage these statements, i.e. create, update and delete which statements show up in each section when editing a report.

Providers also have the ability to validate and correct errors that may have occurred during the testing.

Providers can enter information to identify the patients problems and concerns and they can provide a brief description of it.

Providers are able to describe what is going on with the patient and why they are experiencing what is going on.

Providers can provide the diagnosis or reason for the patient's admission, their medical status, and history. They can also determine the reason or context of the patient's visit, and can enter their current assessment and medical findings on what the problem is based.

Providers can enter what is required, how urgent, and what action needs to be taken.

All audio recorded for speech recognition may be saved. Providers have the ability to listen to the audio and correct the recognition results. Reviewed results are used to train a machine learning algorithm to indicate correct and incorrect answers. The machine learning algorithm detects frequent speech recognition errors for a given grammar and tries to predict corrections.

Providers also have the ability to have the speech recognition audio to other speech recognizers and they can then select which recognition they would like to be used for scoring.

Some trials require classification of recognized words, such is the word an animal. Providers have the ability to add or remove classifications In an embodiment, all audio used for speech recognition may be recorded and stored for future analysis, testing and validation. It is possible some speech recognizers may perform better in some instances than in others. For example, one speech recognizer may perform poorly with numbers, whereas another speech recognizer performs very well. It may be advantageous for each implementation of a test to utilize a different speech recognizer. This may also be used to support the largest number of languages.

The system may enable voice commands, such as pause, help, done, etc. The system may handle interruptions, .e.g, by using an algorithm detecting a sequence of speech that is neither voice commands nor voice responses that are expected as responses to the most recent question in the test. In an embodiment, the algorithm can further be improved with machine learning, by taking audio that we identify as interruptions and using it as data to train a Turing machine learning algorithm.

In an embodiment, the system may determine how long to wait after a person finishes speaking before moving to the next step. This occurs in a digit span test, it is determined whether to move to the next step once a user has responded. If the user has responded correctly, the system move to the next step. If they speak an equal or larger number of digits, they system also moves to the next step after a timeout. If the user speak fewer digits, the system moves after a timeout. The timeout is a constant +a variable. The variable portion is determined by calculating the rate of speech over time for the user and keying the results into a range of values.

Speech recognition can be verified for a patient session. This means the audio files from the session are recognized by several different speech recognizer to improve results. Speech recognition can also be corrected by an administrator, by listening to the audio files for a session and updating the results.

An automated tester that can play back past neuropsychological sessions may be used to test the system. The automated tester may use all data recorded, including audio files, data entered, timings, etc., to play a session back to test the system. The automated tester may listen to the audio from our system, recognize what is being requested, and play back the corresponding audio from the session. This may be used as a diagnostic tool to diagnose any issues with the system that may occur in the field. A test suite may be developed to validate software prior to releases.

Furthermore, while the traditional pen and paper testing can only handle a relatively small testing population, all with the need to travel to a doctor's office and personal interaction, the embodiments described above can be done in the user's home, and provide and save thousands of test results that be stored and analyzed by AI and machine learning modules, possibly providing much greater information in the field.

The above-described embodiments provide a highly-specific set of operations that provide a clear technical benefit (e.g., faster processing, allow patients to take the battery of tests in the solitude, and the ability to carry out tasks that were previously unworkable, e.g. analyze large number of test results.).

The embodiment described above solve a particular technical problem of enabling home testing and recite discrete validation steps that can be taken to obtain this solution.

The foregoing method descriptions and diagrams/figures are provided merely as illustrative examples and are not intended to require or imply that the operations of various aspects must be performed in the order presented. As will be appreciated by one of skill in the art, the order of operations in the aspects described herein may be performed in any order. Words such as "thereafter," "then," "next," etc. are not intended to limit the order of the operations; such words are used to guide the reader through the description of the methods and systems described herein. Further, any reference to claim elements in the singular, for example, using the articles "a," "an," or "the" is not to be construed as limiting the element to the singular.

Various illustrative logical blocks, modules, components, circuits, and algorithm operations described in connection with the aspects described herein may be implemented as electronic hardware, computer software, or combinations of both. To clearly illustrate this interchangeability of hardware and software, various illustrative components, blocks, modules, circuits, operations, etc. have been described herein generally in terms of their functionality. Whether such functionality is implemented as hardware or software depends upon the particular application and design constraints imposed on the overall system. One of skill in the art may implement the described functionality in varying ways for each particular application, but such implementation decisions should not be interpreted as causing a departure from the scope of the claims.

The hardware used to implement various illustrative logics, logical blocks, modules, components, circuits, etc. described in connection with the aspects described herein may be implemented or performed with a general purpose processor, a digital signal processor ("DSP"), an application specific integrated circuit ("ASIC"), a field programmable gate array ("FPGA") or other programmable logic device, discrete gate logic, transistor logic, discrete hardware components, or any combination thereof designed to perform the functions described herein. A general-purpose processor may be a microprocessor, a controller, a microcontroller, a state machine, etc. A processor may also be implemented as a combination of receiver smart objects, e.g., a combination of a DSP and a microprocessor, a plurality of microprocessors, one or more microprocessors in conjunction with a DSP core, or any other such like configuration. Alternatively, some operations or methods may be performed by circuitry that is specific to a given function.

In one or more aspects, the functions described may be implemented in hardware, software, firmware, or any combination thereof. If implemented in software, the functions may be stored as one or more instructions (or code) on a non-transitory computer-readable storage medium or a non-transitory processor-readable storage medium. The operations of a method or algorithm disclosed herein may be embodied in a processor-executable software module or as processor-executable instructions, both of which may reside on a non-transitory computer-readable or processor-readable storage medium. Non-transitory computer-readable or processor-readable storage media may be any storage media that may be accessed by a computer or a processor (e.g., RAM, flash, etc.). By way of example but not limitation, such non-transitory computer-readable or processor-readable storage media may include RAM, ROM, EEPROM, NAND FLASH, NOR FLASH, M-RAM, P-RAM, R-RAM, CD-ROM, DVD, magnetic disk storage, magnetic storage smart objects, or any other medium that may be used to store program code in the form of instructions or data structures and that may be accessed by a computer. Disk as used herein may refer to magnetic or non-magnetic storage operable to store instructions or code. Disc refers to any optical disc operable to store instructions or code. Combinations of any of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed aspects is provided to enable any person skilled in the art to make, implement, or use the claims. Various modifications to these aspects will be readily apparent to those skilled in the art, and the generic principles defined herein may be applied to other aspects without departing from the scope of the claims. Thus, the present disclosure is not intended to be limited to the aspects illustrated herein but is to be accorded the widest scope consistent with the claims disclosed herein.

The invention claimed is:

1. A method comprising:
providing a questionnaire for a patient to perform on a test equipment including a screen,
a voice user interface including a microphone, speaker, and voice processing module, and network connection;
performing a pre-test validation operation to determine suitability of a test environment, the test equipment, and a capability of the patient to perform one or more neuropsychological tests;
providing one or more neuropsychological tests for the patient to perform;
receiving user responses to the one or more neuropsychological tests via the voice user interface;
performing a neurological assessment based on the user responses; and
providing a score representative of the neurological assessment.

2. The method of claim 1, further comprising:
dynamically altering the questionnaire during patient performance of the questionnaire.

3. The method of claim 1, further comprising:
receiving video information representative of the test environment;
performing video analysis on the received video information; and
determining whether the video information indicates meeting environment criteria.

4. The method of claim 1, further comprising:
receiving a recording of audio played on the test equipment; and
determining a level of noise and/or distortion in the recording.

5. The method of claim 1, further comprising:
providing pre-determined text or audio to the test equipment for the patient to repeat;
receiving an audio recording of the patient repeating the pre-determined text or audio; and
performing a speech recognition operation to transform the audio recording to text; and
comparing the pre-determined text or audio to the recognized speech text to determine how accurately the patient repeated the pre-determined text or audio.

6. The method of claim 1, wherein the neuropsychological tests include at least one of a verbal test, a visual test, a drawing test, and a block test.

7. The method of claim 1, wherein the score representative of the neurological assessment is indicative of a risk of the patient for developing Alzheimer's disease.

8. A neuropsychological assessment tool comprising:
a pre-test validation module including a speaker, microphone, screen a video camera, and user input device,
wherein the pre-test validation module is operative to determine suitability of a test environment, a test equipment, and a capability of a patient to perform one or more neuropsychological tests;
a test performance module operative to provide one or more neuropsychological tests for the patient to perform and record user responses to said tests;
an assessment module operative to determine a neurological assessment based on the user responses; and
a scoring module operative to generate a score representative of the neurological assessment.

9. The neuropsychological assessment tool of claim 8, wherein the pre-test validation module is further operative to:
receive video information representative of the test environment;
perform video analysis on the received video information; and
determine whether the video information indicates meeting environment criteria.

10. The neuropsychological assessment tool of claim 8, wherein the pre-test validation module is further operative to:
receive a recording of audio played on the test equipment; and
determine a level of noise and/or distortion in the recording.

11. The neuropsychological assessment tool of claim 8, wherein the pre-test validation module is further operative to:
provide pre-determined text or audio to the test equipment for the patient to repeat;
receive an audio recording of the patient repeating the pre-determined text or audio;
perform a speech recognition operation to transform the audio recording to text; and
compare the pre-determined text or audio to the recognized speech text to determine how accurately the patient repeated the pre-determined text or audio.

12. The neuropsychological assessment tool of claim 8, wherein the neuropsychological tests include at least one of a verbal test, a visual test, a drawing test, and a block test.

13. The neuropsychological assessment tool of claim 8, wherein the score representative of the neurological assessment is indicative of a risk of the patient for developing Alzheimer's disease.

14. The neuropsychological assessment tool of claim 8, further comprising recognition of voice including at least one of pause, help, and done.

15. The neuropsychological assessment tool of claim 14, wherein the pre-test validation module is further operative to detect a sequence of speech that is neither voice commands nor voice responses that are expected as responses to the most recent question in the test.

* * * * *